United States Patent [19]

Slaski

[11] Patent Number: 5,141,434
[45] Date of Patent: Aug. 25, 1992

[54] DRILL

[76] Inventor: Krzysztof Slaski, 9113 Kopping La., Hickory Hills, Ill. 60457

[21] Appl. No.: 627,211

[22] Filed: Dec. 13, 1990

[51] Int. Cl.⁵ .............................................. A61C 3/02
[52] U.S. Cl. ..................................... 433/165; 433/118; 82/1.3
[58] Field of Search ............... 433/118, 121, 122, 123, 433/125, 165, 166; 408/158, 160, 172, 173, 178; 82/1.3

[56] References Cited

U.S. PATENT DOCUMENTS

| | | | |
|---|---|---|---|
| 2,649,001 | 8/1953 | Fennell | 408/158 |
| 3,058,218 | 10/1962 | Kleesattel et al. | 32/27 |
| 3,587,385 | 6/1971 | Orend | 82/1.3 X |
| 3,992,780 | 11/1976 | Herskovits | 32/10 A |
| 4,021,920 | 5/1977 | Kirschner et al. | 433/165 |
| 4,179,810 | 12/1979 | Kirsch | 433/75 |
| 4,279,598 | 7/1981 | Scheicher | 433/173 |
| 4,611,516 | 9/1986 | Hochmuth et al. | 408/158 X |
| 4,712,951 | 12/1987 | Brown | 408/158 |

FOREIGN PATENT DOCUMENTS

| | | | |
|---|---|---|---|
| 3042123 | 6/1982 | Fed. Rep. of Germany | 82/1.3 |
| 3410967 | 10/1985 | Fed. Rep. of Germany | 408/158 |

Primary Examiner—Gene Mancene
Assistant Examiner—Nicholas D. Lucchesi

[57] ABSTRACT

An improved drill for creating oval openings in the jawbone for a tooth to be implanted therein. The drill includes movable cutters that cut an oval shape that matches the cross section of the oval implant by being rotatably driven and performing very fine cuts with movable cutters on an initial pilot hole in the bone.

19 Claims, 5 Drawing Sheets

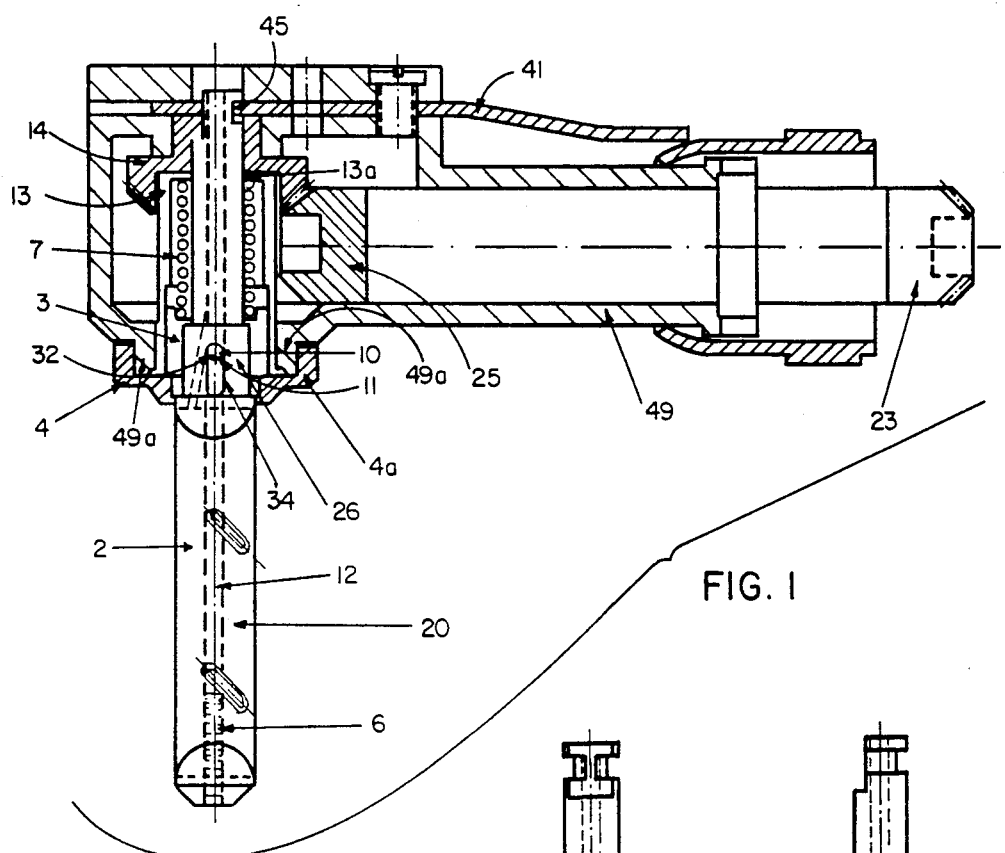
FIG. 1
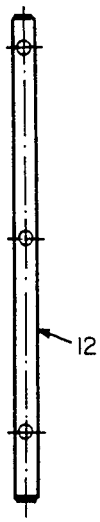
FIG. 4
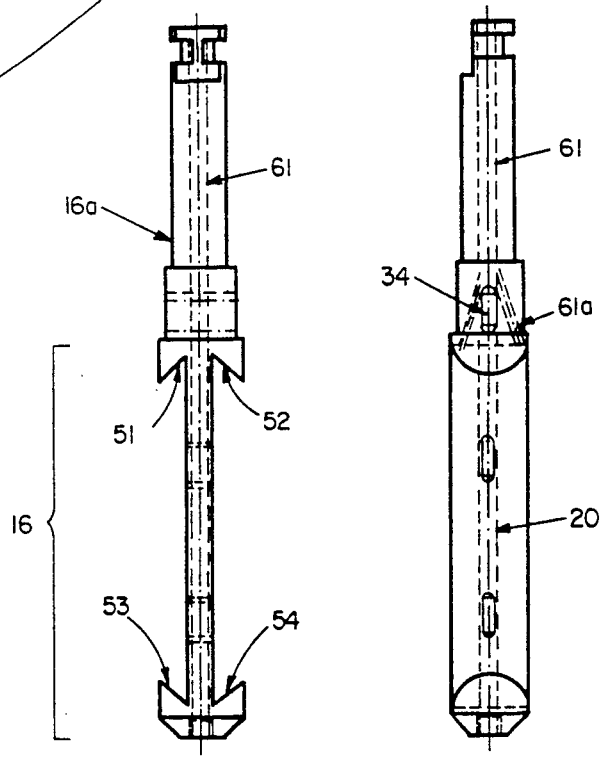
FIG. 2
FIG. 3

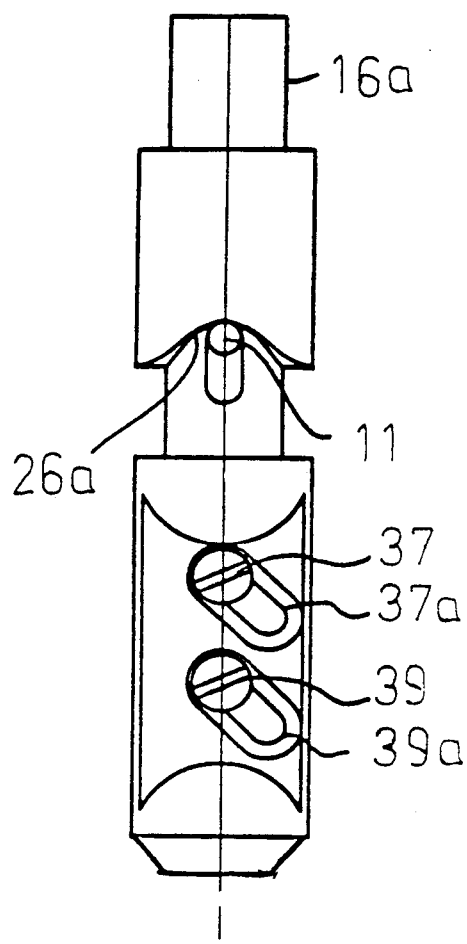
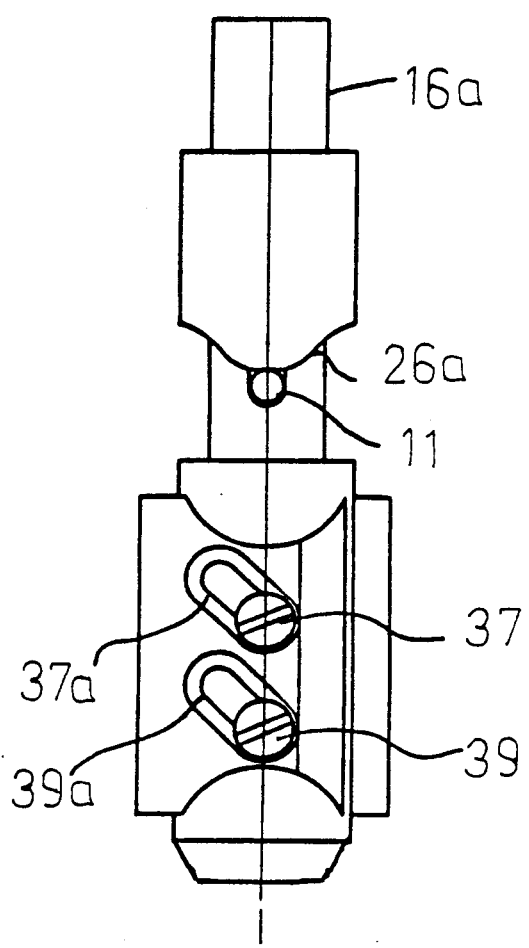
FIG.5  FIG.7
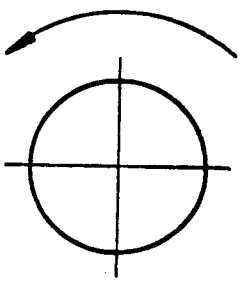
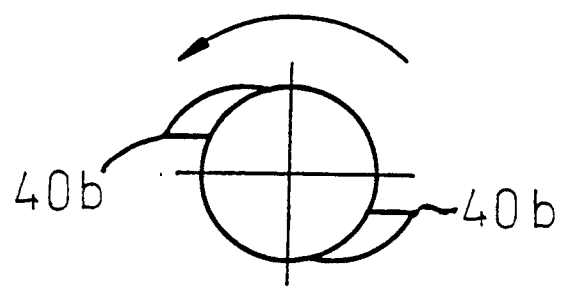
FIG.6  FIG.8

DRILL

BACKGROUND

The present invention relates to a drilling device for cutting an elliptical opening in the jawbone in order to receive a tooth implant which has an implant holder that is implanted in the elliptical opening for supporting it. Once a substantially circular pilot opening is cut, it is advantageous to precisely cut a substantially elliptical opening so that it fits snugly with an elliptically cross-sectioned implant in order to guard against rotation of the implant as well as to have a broader surface for osteointegration.

Jaw implants in the jawbone are common and it has been found that one of the best shapes for anchoring the implant in the bone is by means of having a substantially elliptical or oval opening for receiving the implant. Accordingly, it is desirable to use a substantially elliptical or oval cross section in the implant; by being oval or substantially elliptical, with snug fit in the bone receptacle, the implant has the best chance of stimulating making a firm and stable connection with the cortical bone.

One of the disadvantages of using an oval cross section is that it is difficult to precisely cut the bone to form a precise oval opening that fits snugly with the implant.

It is therefore an object of this invention to provide an improved drill and an improved method of precisely drilling a substantially elliptical or oval hole in the cortical bone for anchoring tooth implants so that osteointegration will occur and the implant will have a firm seat and offer sufficiently great resistance to any forces that might ordinarily dislodge the implant.

Another object of the invention is to provide a very precise elliptical or oval opening to receive an implant having a cross section that is elliptical and has snug and intimate relation with the jawbone in order to prevent motion between the bone and the implant during the healing period.

A feature of the invention includes providing an adjustable drilling head whereby optimum positioning of the drilling head can be effected to more easily work in the patient's mouth.

One other feature of the invention includes having the cutters yieldingly operate by allowing them to retract when a force is encountered in contact with the bone, whereby trauma to the bone is reduced and the bone can be gradually cut with small shavings being removed therefrom.

The drilling device of this invention is comparable in size to a conventional surgical drilling head and is powered conventionally and has water flowing through to cool off the bone being cut as well as cleanse it. Also, the drilling instruments made in accordance with this invention are such that they can be associated with a number of conventional driving devices as will be shown and explained herein.

IN THE DRAWINGS

Other objects, advantages and features of this invention will become readily apparent, and while the main features of this invention will be particularly pointed out in the claims, the invention itself and the manner in which it may be made and used may be better understood by referring to the following description taken in connection with the accompanying drawings wherein like characters of reference indicate corresponding parts throughout:

FIG. 1 is a cross-sectional view of an assembly of the surgical drill;

FIG. 2 is a side elevational view of a drill bit with its cutting blades removed;

FIG. 3 is a side elevational view of FIG. 2;

FIG. 4 is an enlarged view of a pusher rod that is inserted into the axis of the drill bit;

FIG. 5 is a schematic side elevational view of the drill bit pictured showing the cam surface in its extreme position prior to actuating the movable blades;

FIG. 6 is a bottom view of the drill bit;

FIG. 7 is a schematic side elevational view of the drill bit after the cam surface has actuated the cutters to their fully open, extreme position;

FIG. 8 is a bottom view of a drill illustrating the cutters in their fully open, extreme position;

FIGS. 17 and 18 represent a repetition of FIGS. 6 and 8.

DETAILED DESCRIPTION OF THE EMBODIMENT

Figure 13:
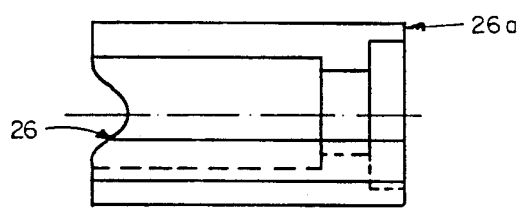
FIG. 13 is a half-sectional view of the cam bushing.
Figure 13A:
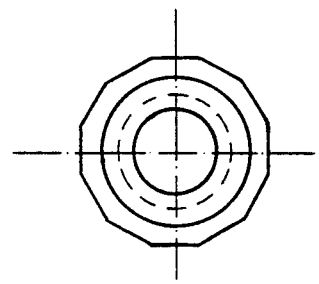
FIG. 13a is a side elevational view of the cam bushing in FIG. 13.
Figure 12:
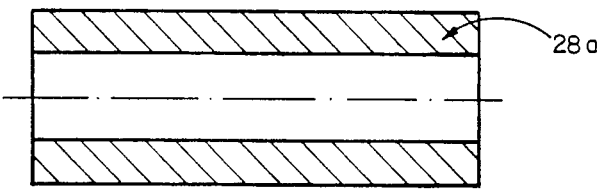
FIG. 12 is an enlarged view of a cam follower, a pair of which are shown with the cam surface of the cam bushing in FIG. 10.

Referring to FIG. 1, the drill head 21 is shown in half sectional. The drill head 21 has a drive shaft 23 which is rotatably driven and has a driving pinion gear 25 associated with bevel gear 14 that has the upper portion 16a of the drill bit 16 keyed therein. The bevel gear 14 in turn rotates the upper portion 16a of the drill bit, which in turn rotates the remaining portion of the drill bit 16. As seen from FIG. 1, the drill bit 16 has a curved cam surface 26 that is part of a cam bushing 26a shown in FIG. 13. The followers 28, 28a, shown in FIG. 12, are associated with a pusher rod 12 on each side of the drill bit 16 by means of the driving pin or follower bar 11 and the followers 28, 28a moving in and being constrained to move vertically by the parallel slot 34 formed in the upper portion 16a of the drill bit 16, as seen from FIGS. 1 and 10.

In FIG. 1, the pusher rod 12 is shown inserted in the axis opening 20 of the drill bit 16 and is associated therewith by means of three pins which include the driving pin 11 already mentioned, as well as the slat cutter pins 37 and 39, each also respectively constrained to move in the diagonal slots 37a and 39a as well.

Figure 18:
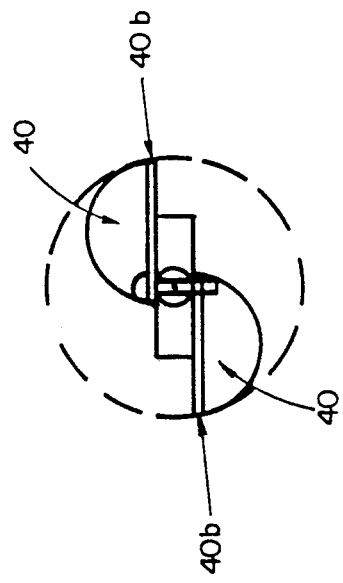
FIG. 18 is a bottom view of the drill bit with the movable cutter slats of the drill bit at their "fully open" position after being actuated by the cam surface.
Figure 17:
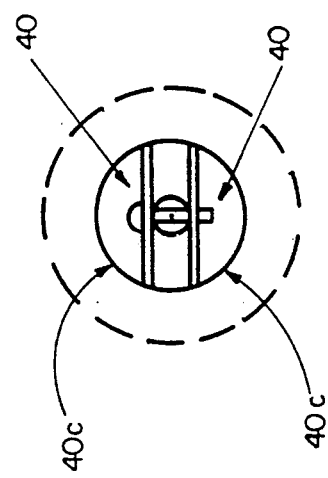
FIG. 17 is a bottom view of the drill bit showing the movable cutter slats in their "fully closed" position prior to being actuated by the cam surface.
Figure 10:
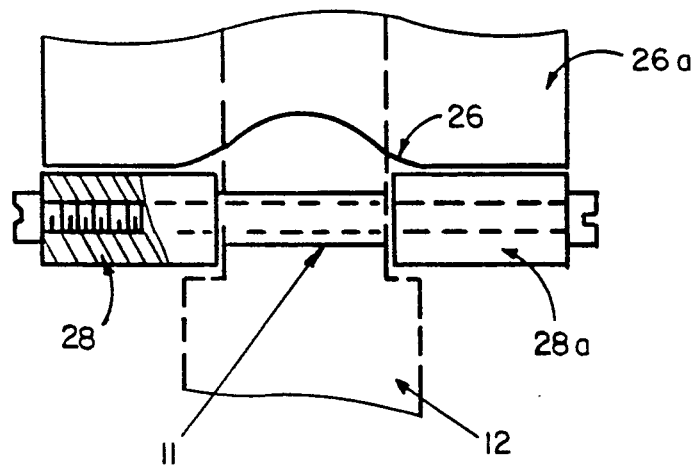
FIG. 10 shows the cam, follower and driver pin or follower bar 11 that actuates a pusher rod and, in turn, actuates the movable cutting blades of the drill bit.

Thus, when the followers 28, 28a as pictured on each side of the parallel slot 34 in FIG. 10 are actuated by the curved cam surface 26, the pusher rod 12 is caused to move downward against the force of the spring 6 and, in turn, move the slat cutter pins 37, 39 in the diagonal slots 37a, 39a while being constrained by the pusher rod 12 to move downward. This causes the slat cutters 40 to be gradually moved outward until the extreme position of the cutters is reached, as illustrated in FIGS. 8 and 18. In this position, the blade edges 40b are at their farthest distance between each other.

As seen from FIG. 1, the upper portion 16a of the drill bit has a groove 45 on the end thereof that makes contact with a plate 47 that restrains the drill bit 16 from moving downward and allows it to rotate as it is being rotatably actuated by the bevel gear 14. The sleeve 13 has an opening 13a that receives the upper portion 16a of the drill bit 16 at the top thereof and has a lower portion that rests on the nut 4 which has threads therein so that it is threadably fastened and held firm to the head piece 49 while the drill bit 16 rotates.

The head piece 49 has a nut contacting portion 49a that makes contact with the inside 4a of the nut 4.

The bevel gear 14 is driven by the driving pinion gear 25 and the drive shaft; and the upper portion 16a of the drill bit is keyed into the bevel gear 14, as shown in FIG. 1. A cam bushing 3, which is slipped into and fits with the inside polygon opening 13b of the sleeve 13 where it is pressed against the spring 7 is also held in place by the nut 4. This arrangement enables the drill to be journalled on the inside opening of the cam bushing 26a whose curved cam surface 26 rotates and contacts the followers 28 and 28a as seen from FIGS. 1, 5 and 7.

As can be seen from FIGS. 5 and 7, the curved cam surface 26 has two extreme positions "fully open" and "fully closed," as shown. The curved cam surface 26 is shaped like a sinoisoidal wave, as illustrated in FIG. 6, to gradually move the drive pin 11 which has the followers 28, 28a thereon from their "fully closed," extreme position in FIGS. 5 and 6 to their "fully open" position. The path of the cam 26 and followers 28, 28a is laid out in FIG. 16. When the sinoisoidal wave is at its highest peak, this represents the "fully closed" position when the slat cutters 40, 40a are in their position shown in FIGS. 5 and 6. When the wave is in its lowest position, this represents the "fully open" position where the slat cutters have been actuated to the position shown in FIGS. 7 and 8.

In order to fully appreciate how the movable slat cutters 40 are mounted in the drill bit, FIGS. 2 and 3 show the drill bit without the slat cutters 40 mounted therein. Thus, when assembling the slat cutters 40 with the drill bit, they are slipped into the inclined portions 51, 52, 53 and 54 so that the inclined slat portions 56, 57 on each of the slat cutters 40 dovetail therewith to form a substantially uniform periphery, as seen in FIG. 6. The movable slat cutters 40 are held in place by the pins 37, 39 that move in the slots 37a, 39a formed in each of the slat cutters 40. The drill bit has the inclined portions 51, 52, 53, 54 for receiving one of the slat cutters 40 on each side thereof. The flat section 40a of the slat cutters 40 are sized to harmoniously fit into the cavities created by the angular portions 51, 52, 53, 54 of the drill bit. As mentioned hereinbefore, the curved portions 40c of the slat cutters 40 are shaped to conform to the periphery of the drill bit when the slat cutters are in place so that the bottom of the drill bit would appear as a circular when the movable slat cutters 40 have been moved to their fully closed position, as seen in FIG. 6.

It must be realized that the slat cutters 40 are moved from their fully closed position (FIG. 6) to their fully opened position (FIG. 8) gradually, while the drill bit 16 is rotating. Also, the slat cutters 40 are yielding in the sense that they will be caused to move and withdraw against the bias of the spring 7.

Once the pilot opening is cut and it is desired to cut the oval hole with the cutters, the drill enables the cutters to cut very gradually by being yieldingly mounted by means of the springs 6 and 7. The slat cutters 40, by being able to react when they encounter resistance, decrease the trauma created by cutting the oval. By having the slat cutters 40 in effect by yieldingly urged by the cam surface 26, they are able to sense resistance at the bone and yield and enable the shaving to occur gradually. Thus, there is a spring 7 that biases the cam followers 28, 29 so that when the slat cutters 40 are encountering resistance the curved cam surface moves upward and yields to the resistance caused by the bone to create gradual shavings as the drill bit is being rotated in that situation.

The position of the pusher bar 12, as shown in FIG. 1, illustrates the followers 28, 28a, in the fully closed position as in FIG. 5. Also, the cutter pins 37 and 39, which associate the cutters 40 with the pusher bar 12 as seen in FIG. 1, are correspondingly positioned in their extreme, "fully closed" position at the point illustrated in FIG. 1. When the drill bit 16 is caused to rotate, liquid (shown in phantom in FIG. 3) is forced down through the center opening of the drill bit in order to cool off and cleanse the bone being cut.

Figure 11:
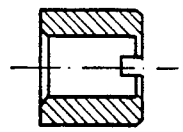
FIG. 11 is an enlarged view of a nut that holds the driver pin and cam followers in place.

As the drill bit 16 rotates, the cam surface 26 of the cam bushing 3 has contact with the followers 28, 28a and by being spring biased by the spring 7, acts as a shock absorber in creating the constant force mentioned previously since the bushing will be caused to yield upward and compress the spring 7 to create a cushion effect that enables gradual shavings to be cut from the oval opening. As seen from FIG. 10, the follower portions 28 and 28a, in being on both sides of the drill bit slot 34, comes in contact with the cam surface 26 which is also on the other side of the drill bit slot 34 so that when the drill is rotating, the same cam surface 26 is working on the followers 28, 28a on both sides of the drill bit. As seen from FIG. 13, the cam surface 26 is formed on the cam bushing 3. The nut shown in FIG. 11, fastens the followers 28, 28a and the pusher rod 12 and the drill bit together as seen from FIG. 10.

Figure 14:
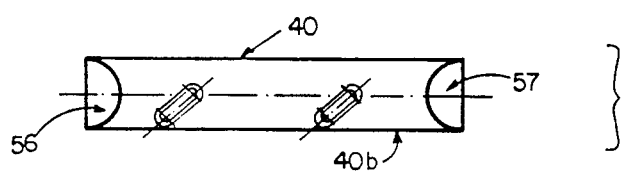
FIG. 14 is a top view of one of the movable cutter slats.
Figure 15:
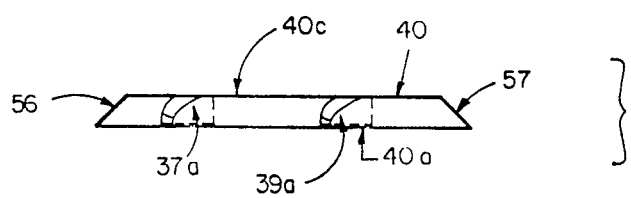
FIG. 15 is a side elevational view of FIG. 14.

The diagonal slots 37a, 39a of the slat cutters 40 constrain the pins 37, 39, as seen from FIGS. 5, 7 and 14; and in gradually moving along the diagonal line of the slots the slat cutters cut an oval surface when the cam surface 26 is shaped substantially as a sine wave and is urging the pusher bar 12 straight downward along the central axis of the drill bit. The combination of motions created include rotation of the drill bit 16 while the slat cutters 40 are being actuated outward by means of the pins being forced along the diagonal slots while being restrained in the vertical path of the pusher rod 12.

These relative motions enable the drill bit to achieve oval cutting while substantially obeying a mathematical formula which is as follows:

$$F_{(\alpha, P)} = r - M(1 - \cos 2\alpha)$$

Figure 19:
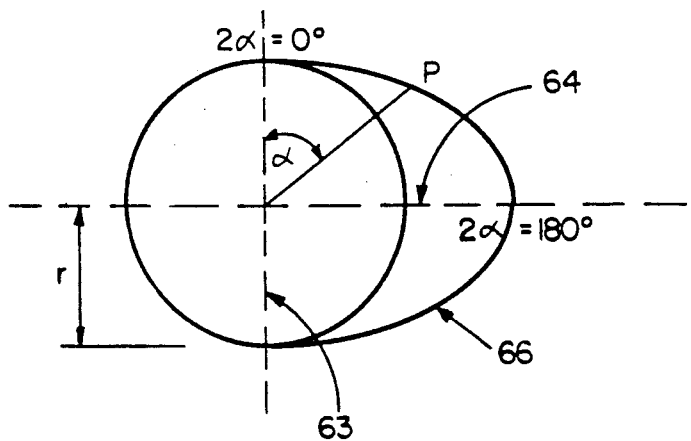
FIG. 19 is a plane view of half of an oval shaped function that approximates the oval shaped cavity that can be cut by said drill bit.

In this formula, 2r, as seen in FIG. 19, equals the diameter of the drill bit which is the short axis 63 of the oval 66. The formula above describes distance from the center of rotation of any point P on the perimeter of the shape cut, where $\alpha$ is an angle the drill bit rotated; and M is $\frac{1}{2}$ amplitude of the cam curve. The long axis of the oval 66 equals 2r+4M.

Because the slots 37a, 39a are at a 45° angle to the long axis of the drill bit, each movable cutter slat 40 is extended the exact amount of the downward travel of the pusher bar 12. Accordingly, the motion of the cutter slats' blades edges 40b are following and depicting the motion of the curved cam surface which is expressed in the formula as $F_{(\alpha, P)}$.

Figure 16:
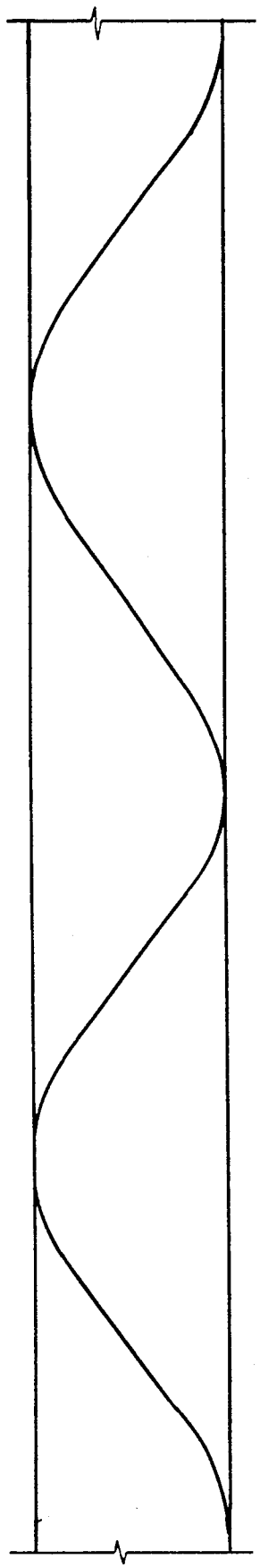
FIG. 16 is a sinoisoidal wave form representing the positions of the cam surface as the drill bit rotates.
Figure 20:
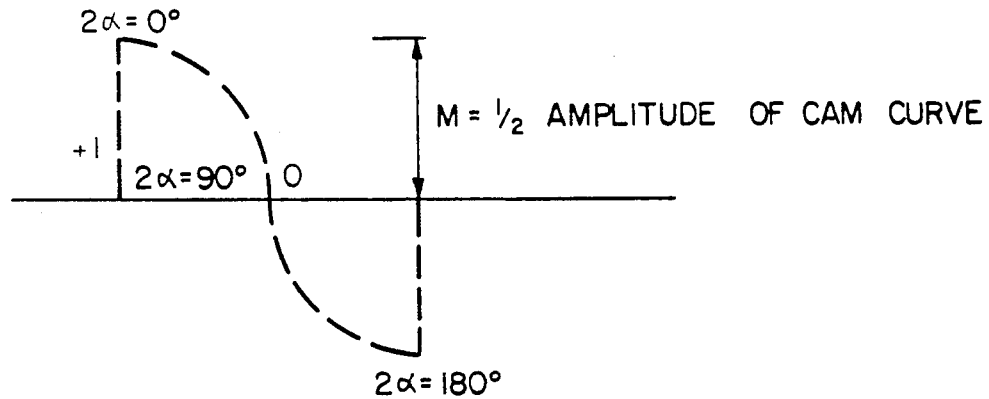
FIG. 20 shows a fragment of the cam curve expressed by cosine $2\alpha$, where $\alpha$ is an angle of drill bit turn.

Since, as seen from FIG. 16, two cosine curves have been preferably used for the complete shape of the cam, for each angle turn of the drill bit, the drill bit followers 28, 28a travel the equivalent of $2\alpha$ on this cosine curve. Thus, as seen from FIGS. 19 and 20, at point 0°, the movable slat cutter blades are fully retracted and in their closed position. When the drill bit is rotated 90° the slat cutters 40a are fully extended. This corresponds to the cosine 180° where the followers 28, 28a are at the lowest point of the cam as seen in FIG. 20.

The statements above can be proven by plugging in the parameters of 0°, 45° and 90° in the above formula for to define the position of point P of the perimeter being cut:

If $\alpha = 0°$ $\cos 2\alpha = 1 F_{(\alpha, P)} = r - (1-1)M = r$

If $\alpha = 45°$ $\cos 2\alpha = 0 F_{(\alpha, P)} = r - (1-0)M = r - M$

If $\alpha = 90°$ $\cos 2\alpha = -1 F_{(\alpha, P)} = r - (1[-1])M = r - 2M$

Figure 9:
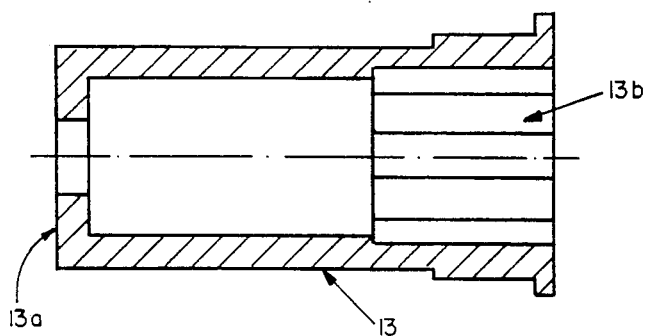
FIG. 9 is a half-sectional view of a sleeve that encases a spring for the drill.
Figure 9A:
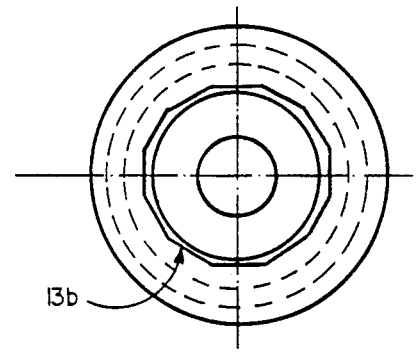
FIG. 9A is a side elevational view of the sleeve in FIG. 9.

In FIGS. 2 and 3, the phantom lines shown along the center 61 of the drill bit have tributaries 61a leading to the slat cutters 40 through the drill bit 16 and indicate water channels to guide water, under pressure, through the drill bit in order to wash and cool the slat cutters 40. Where it is desired to re-position the head of the drill at a different angle with respect to the drill bit 16, the sleeve 13 (as illustrated in FIGS. 1, 9 and 9a) can be rotated and fixed in that position to thereby enable an easier access to the drilling site in a patient's mouth.

The cam bushing's 3 outer periphery has a matching outer polygonal surface 3a to the inner polygonal surface 13b of the sleeve 13.

Thus, the invention has accomplished the objects stated herein by not only providing an improved drilling device, but also an improved process for enabling cutting the jaw bone in order to receive an implant.

What is claimed:

1. In a drilling device used for cutting an oval cross section of a certain cross section cavity in the bone that is intended to fit snugly with the oval cross section of a tooth implant when a pilot hole has been initially formed in said bone,
   including a rotatably driven drill bit,
   the improvement comprising:
   movable cutter means associated with said drill bit for rotation spring biasing force means with said drill bit around the center of said drill bit,
   and a curved cam surface operatively associated with said drill bit and said spring biasing force means to actuate said movable cutter means to gradually and yieldingly move outward from said drill bit in response to the bone resistance and curvature of said cam surface when said drill bit rotates, and has been totally immersed in said pilot hole,
   whereby said oval cavity can be cut by removing bone from said cavity during rotation of said drill bit and said movable cutter while said drill bit is aligned with the intended center of said oval cavity and is totally immersed in said pilot hole.

2. The drilling device according to claim 1 wherein a vertically extending pusher rod is associated with said movable cutter means,
   said pusher rod being constrained to move vertically,
   follower means operatively associated with said curved cam surface and said pusher rod to move vertically in response thereto when said drill bit is rotatably driven,
   whereby vertical movement of said pusher rod in response to said cam surface actuating said follower means creates gradual movement outward of said movable cutter means.

3. The drilling device according to claim 2 wherein said pusher rod is constrained to move within a certain vertical distance.

4. The drilling device according to claim 2 wherein said movable cutter means has angular slot means that constrain the movement of said cutter means.

5. The drilling device according to claim 4, wherein said angular slot means are at a 45° angle with respect to said pusher rod, whereby the vertical travel of said pusher rod is equal to the outward travel of said movable cutter means.

6. The drilling device according to claim 2 wherein a cam bushing has said cam surface formed on the bottom thereof and said spring biasing force means is a spring means biasing it downward,
   whereby said movable cutter means has a constant yielding force applied to it by said cam surface that enables said movable cutter means to yield if the bone resists said movable cutter means beyond the force applied by said spring biasing means.

7. The drilling device according to claim 6 wherein there is a cam bushing that has said curved cam surface formed on the bottom thereof and a sleeve receives said cam bushing at the bottom thereof and houses said spring biasing means.

8. The drilling device according to claim 8 wherein said cam bushing has a polygonal shaped periphery and said sleeve has a polygonal shaped inside surface that fits with said polygonal periphery of said cam bushing,
   whereby the repositioning of said drilling device with respect to said drill bit can be accomplished on the basis of changing the angular position of said cam bushing with respect to said sleeve.

9. The drilling device according to claim 2 wherein said drill bit has a follower bar associated with said pusher rod and extending through a vertical slot in said drill bit on both sides thereof that constrains the vertical movement of said pusher rod, and said follower means are associated with said pusher rod on each side of said drill bit by said follower bar to enable said follower means to contact said cam surface on opposite sides of said drill bit while said drill bit is rotating.

10. The drilling device according to claim 1, wherein said drill bit has cavities formed therein for receiving said movable cutter means, said movable cutter means include cutter slats that fit in said cavities when said cutter means are in their fully closed position, and said cutter slats have angular ends that are slidably associated with said drill bit cavities to enable said cutter slats to move in response to said drill bit's relative position with respect to said cam surface.

11. The drilling device according to claim 10 wherein said cutter slats have flat surfaces on the bottom and have curved surfaces on the top, and said flat surfaces are slidably mounted with respect to said drill bit to move in response to said cam surface.

12. The drilling device according to claim 11 wherein said curved surfaces conform with and are coincident with the periphery of said drill bit when said drill bit and cutter slats are in the fully closed position.

13. The drilling device according to claim 12 wherein said drill bit has substantially vertical cavities for receiving said pusher rod and allowing liquid under pressure to be circulated in said drill bit to cool off and cleanse said bone.

14. The drilling device as defined in claim 1 wherein said cam surface curve has the approximate shape of two cosine curves around its perimeter.

15. The drilling device as defined in claim 14 wherein the amplitude of said curve of said cam surface approximates two times the radius of the drill bit.

16. The drilling device as defined in claim 15 wherein the long axis of said oval cavity approximately equals the diameter of said drill bit plus two times the distance of the edge of the cutter means from said drill bit center when said cutter means is in its fully opened position.

17. The drilling device as defined in claim 16 wherein the function of the curve of the oval cavity is substantially expressed as follows:

$$F_{(a, P)} = r - (1 - \cos 2a) M$$

where:

$r$ = radius of drill bit;
$a$ = angle of turn of the drill bit;
$M = \frac{1}{2}$ the amplitude of the cosine curve of the cam surface;
$P$ = point on the perimeter of ultimate oval cut.

18. In a process utilizing drill bit for cutting a cavity of oval cross section in the bone that snugly conforms to the cross section of an intended implant, wherein movable cutter means are rotatably driven by the drill bit comprising the steps of:

a. drilling a circular pilot hole in the bone;

b. forming an oval shaped hole in the bone by mans of fully immersing said drill bit in said pilot hole and actuating the cutter means to move gradually outward from said drill bit in order that rotation of said drill bit against said bone causes said cutter means to gradually remove bone from said cavity to define a cavity of oval cross section.

19. In a process such as defined in claim 18, wherein said drill bit has a circular bottom that is sized to engage and anchor the lower end of the drill bit in said pilot hole, while drilling of said oval shaped hole occurs:

the step of positioning said bottom of said drill bit and engaging and anchoring it by inserting it in said hole until it contacts the bottom of said hole, prior to rotation of the drill bit, whereby said drill bit is precluded from moving off the pilot hole center when said oval shaped hole is formed in said bone.

* * * * *